United States Patent

Iwao et al.

[11] Patent Number: 5,610,169
[45] Date of Patent: *Mar. 11, 1997

[54] PHARMACEUTICAL COMPOSITION CONTAINING SLIGHTLY WATER-SOLUBLE DRUG

[75] Inventors: Toru Iwao; Kenichi Hirai; Nobuo Kondoh; Koichi Yamanouchi; Kazumasa Yokoyama, all of Hirakata, Japan

[73] Assignee: The Green Cross Corporation, Osaka, Japan

[ * ] Notice: The term of this patent shall not extend beyond the expiration date of Pat. No. 5,462,951.

[21] Appl. No.: 474,549

[22] Filed: Jun. 7, 1995

Related U.S. Application Data

[63] Continuation of Ser. No. 115,785, Sep. 3, 1993, Pat. No. 5,462,951, which is a continuation of Ser. No. 672,498, Mar. 20, 1991, abandoned.

[30] Foreign Application Priority Data

Mar. 23, 1990 [JP] Japan ......................... 2-73695

[51] Int. Cl.⁶ ............... A61K 31/44; A61K 31/495; A61K 47/00
[52] U.S. Cl. ............... 514/334; 514/252; 514/332; 514/356; 514/255; 514/333; 514/786; 514/946
[58] Field of Search .................. 514/334, 252, 514/332, 356, 255, 333, 786, 946

[56] References Cited

U.S. PATENT DOCUMENTS

| | | | |
|---|---|---|---|
| 4,595,690 | 6/1986 | Clark et al. | 514/356 |
| 4,690,823 | 9/1987 | Lohner et al. | 514/456 |
| 4,737,506 | 4/1988 | Shimizu et al. | 514/332 |
| 4,880,634 | 11/1989 | Speiser | 514/286 |
| 4,990,337 | 2/1991 | Kurihara et al. | 514/786 |
| 5,124,340 | 6/1992 | Jaffe et al. | 514/356 |

FOREIGN PATENT DOCUMENTS

| | | |
|---|---|---|
| 0023349 | 2/1981 | European Pat. Off. . |
| 0031603 | 7/1981 | European Pat. Off. . |
| 0163178 | 12/1985 | European Pat. Off. . |
| 0163270 | 12/1985 | European Pat. Off. . |
| 0179583 | 4/1986 | European Pat. Off. . |
| 0257616 | 3/1988 | European Pat. Off. . |
| 0319947 | 6/1989 | European Pat. Off. . |
| 0326103 | 8/1989 | European Pat. Off. . |
| 064609 | 4/1982 | Japan . |
| 126819 | 5/1988 | Japan . |

*Primary Examiner*—Marianne M. Cintins
*Assistant Examiner*—Keith MacMillan
*Attorney, Agent, or Firm*—Sughrue, Mion, Zinn, Macpeak & Seas

[57] ABSTRACT

The orally administrable pharmaceutical compositions containing a slightly water-soluble drug, characterized by improved stability and improved absorption of the drug from digestive tract into blood. The use of the compositions of the present invention enables decrease of the dose amount of a slightly water-soluble drug, which eventually leads to alleviation of pains and side effects on the part of patients.

11 Claims, No Drawings

1

PHARMACEUTICAL COMPOSITION CONTAINING SLIGHTLY WATER-SOLUBLE DRUG

This is a continuation of application Ser. No. 08/115,785 filed Sep. 3, 1993 now U.S. Pat. No. 5,462,951 which is in turn a continuation of U.S. application Ser. No. 07/672,498 filed Mar. 20, 1991, abandoned.

BACKGROUND OF THE INVENTION

The present invention relates to orally administrable pharmaceutical compositions containing a slightly water-soluble drug. The pharmaceutical compositions for oral use according to the present invention are based on the characteristic properties of improved absorption From digestive tract into blood and improved stability.

Due to poor absorption of slightly water-soluble drugs, particularly dihydropyridine derivatives and lipoxygenase inhibitors, from digestive tract, there has been a strong demand for the development of pharmaceutical formulations which afford good absorption in clinical applications. In order to improve absorption, addition of an absorbefacient, improvement of dosage form designs, etc. are necessary, and generally employed means of formulation are pulverization of crystals, noncrystallization, addition of surfactants, cyclodextrin inclusion, emulsification, dissolution in polyethylene glycol, vegetable oil, etc., or the like. However, none of these affords sufficient absorption from digestive tract.

In addition, dihydropyridine derivatives are specifically unstable to light, and for this reason, they are prepared into light-resistant preparations or colored preparations and stored in light-resistant containers.

SUMMARY OF THE INVENTION

In an attempt to solve the aforementioned problems, an object of the present invention is to provide compositions containing a slightly water-soluble drug which improve absorption by oral administration. Another object of the invention is to provide compositions wherein an unstable drug such as dihydropyridine derivatives is stabilized therein.

The present inventors have conducted intensive studies to provide effective absorption of a slightly water-soluble drug from digestive tract and found that excellent bio-availability (BA) in oral use and stability of the drug can be achieved when the slightly water-soluble drug is formulated into a non-micelle composition by adding a fatty acid monoglyceride and/or a polyoxyethylenesorbitan fatty acid ester to the slightly water-soluble drug, or formulated into a composition by further adsorbing same onto a porous inorganic substance, and that the thus-obtained composition serves well as a pharmaceutical composition for oral use.

The present invention has been completed on the basis of such findings, and the present invention relates to non-micelle pharmaceutical compositions for oral use wherein a slightly water-soluble drug is dissolved in a fatty acid monoglyceride and/or a polyoxyethylenesorbitan fatty acid ester, and to pharmaceutical compositions for oral use wherein the composition is further adsorbed onto a pharmaceutically acceptable porous inorganic substance.

DETAILED DESCRIPTION OF THE INVENTION

The slightly water-soluble drug in the invention is not particularly limited as long as it has a solubility of 0.1 mg/ml or below in water and is pharmacologically active. Specifically, the slightly water-soluble drug means those which are slightly absorbed by oral administration, have BA (%) of 10 or below, preferably 5 or below, more preferably 3 or below, when orally administered after pulverization with a mortar [into 200 mesh (75 μm) or below] and suspending same in an aqueous solution of 0.5% sodium carboxymethyl-cellulose, and are easily dissolved in a fatty acid mono-glyceride and a polyoxyethylenesorbitan fatty acid ester. They are exemplified by dihydropyridine derivatives and lipoxygenase inhibitors such as caffeic acid derivatives, aromatic unsaturated ketone compounds and substituted stylene derivatives.

As the dihydropyridine derivatives, the following compounds are preferably given. That is, dihydropyridine derivatives of the formula

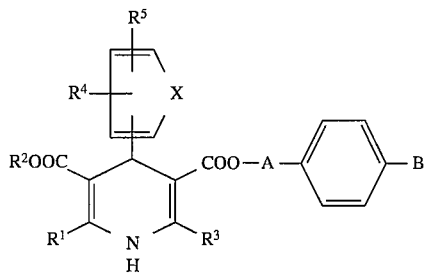

wherein $R^1$, $R^2$ and $R^3$ are the same or different and are an alkyl, a cycloalkyl or an alkoxyalkyl, $R^4$ and $R^5$ are the same or different and are hydrogen atom, a halogen, nitro, a halogenated alkyl, an alkylsulfonyl, a halogenated alkoxy, an alkylsulfinyl, an alkyl, a cycloalkyl, an alkoxy, cyano, an alkoxycarbonyl or an alkylthio wherein $R^4$ and $R^5$ are not hydrogen atoms at the same time, X is a group of vinylene or azomethine, A is an alkylene and B is $-N(R^6)_2$ or

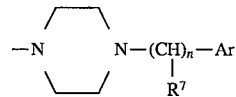

where $R^6$ and $R^7$ are respectively hydrogen atom, an alkyl, a cycloalkyl, an aralkyl, an aryl or pyridyl, Ar is an aryl or pyridyl and n is an integer of 0 to 2, or their acid addition salts (U.S. Pat. No. 4,886,819, EP 257616).

The alkyl represented by $R^1$, $R^2$ or $R^3$ is preferably a lower alkyl having 1 to 6 carbon atoms, with further preference given to that having 1 to 4 carbon atoms. The lower alkyl may have a lower cycloalkyl having 3 to 6 carbon atoms on the alkyl terminal. As the cycloalkyl, a lower cycloalkyl having 3 to 6 carbon atoms is preferable. As the alkoxyalkyl, preferred are those having 3 to 7 carbon atoms.

The substituent represented by $R^4$ or $R^5$ is preferably at the 2- and/or 3-position to the binding site with the dihydropyridine ring. As the halogen at $R^4$ or $R^5$, particularly preferred are fluorine or chlorine atom, and as the alkyl and cycloalkyl, preferred are those mentioned as $R^1$ to $R^3$. The alkoxy and the alkylthio preferably possess a lower alkyl having 1 to 3 carbon atoms.

As the alkoxycarbonyl, there may be mentioned those having 2 to 4 carbon atoms. The halogen in halogenides is exemplified by those mentioned above, and the halogenated alkyl and the halogenated alkoxy may be that where some of the hydrogen atoms are halogenated or all of the hydrogen atoms are halogenated. The alkyl in alkylsulfonyl and alkylsulfinyl includes those exemplified as $R^1$ to $R^3$.

As $R^4$ and $R^5$, preferred are cyano and halogenated alkyl (specifically, trifluoromethyl).

The alkyl and the cycloalkyl represented by $R^6$ and $R^7$ include those exemplified as $R^1$ to $R^3$. Phenyl $C_{1-3}$ alkyl is preferred as the aralkyl, and phenyl and naphthyl are preferred as aryl. These aromatic rings may have the same or different substituents at an optional position. The substituents on the aromatic ring include those mentioned as $R^4$ and $R^5$. The pyridyl includes 2-pyridyl, 3-pyridyl and 4-pyridyl, which may have the substituents mentioned above as $R^4$ and $R^5$.

The alkylene represented by A includes those having 2 to 4 carbon atoms, which may be a straight- or branched-chain.

The aryl and the pyridyl represented by Ar include those exemplified as $R^6$ and $R^7$ and may have the same substituents.

The ring represented by

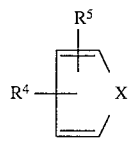

which is the 4-position substituent of dihydropyridine, means a benzene ring when X is vinylene (—CH=CH—) and pyridine when X is azomethine (—CH=N—). An optional position of the ring may bind to the 4-position of the dihydropyridine.

The substituents $R^4$ and $R^5$ are preferably at the ortho- and/or meta-position to a carbon atom binding to the 4-position of the dihydropyridine.

As such compounds, the following can be mentioned.

2-(p-Dimethylaminophenyl)ethyl methyl 2,6-dimethyl-4-(4-cyano-2-pyridyl)-1,4-dihydropyridine-3,5-dicarboxylate and its hydrochloride 2-(p-Dimethylaminophenyl)ethyl methyl 2,6-dimethyl-4-(2-trifluoromethyl-3-pyridyl)-1,4-dihydropyridine-3,5-dicarboxylate and its hydrochloride 2-(p-Dibenzylaminophenyl)ethyl methyl 2,6-dimethyl-4-(4-cyano-2-pyridyl)-1,4-dihydropyridine-3,5-dicarboxylate and its hydrochloride 2-(p-Dibenzylaminophenyl)ethyl methyl 2,6-dimethyl-4-(2-trifluoromethyl-3-pyridyl)-1,4-dihydropyridine-3,5-dicarboxylate and its hydrochloride 2-[p-(4-Benzhydrylpiperadino)phenyl]ethyl methyl 2,6-dimethyl-4-(4-cyano-2-pyridyl)-1,4-dihydropyridine-3,5dicarboxylate and its hydrochloride 2-[p-(4-Benzhydrylpiperadino)phenyl]ethyl methyl 2,6-dimethyl-4-(2-trifluoromethyl-3-pyridyl)-1,4-dihydropyridine-3,5-dicarboxylate and its fumarate 2-[p-(4-Benzhydrylpiperadino)phenyl]ethyl methyl 2,6-dimethyl-4-(3-nitrophenyl)-1,4-dihydropyridine-3,5dicarboxylate and its hydrochloride As tile lipoxygenase inhibitors, examples include compounds of the following formulas ① to ⑦.
① Caffeic acid derivatives of the formula

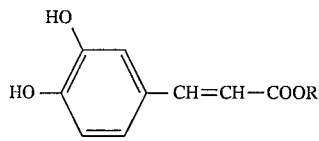

wherein R is an alkyl having 3 to 10 carbon atoms which may be substituted by a halogen atom (U.S. Pat. No. 4,733,002, EP 163270).

The halogen atom as a substituent is preferably chlorine atom. The alkyl substituted by the halogen includes, for example, —CO—O—(CH$_2$)$_3$—CH$_2$—Cl, —CO—O—(CH$_2$)$_3$—CHCl$_2$,

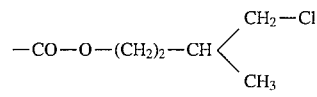

and

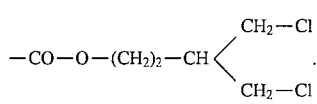

As such compounds, there may be mentioned caffeic acid propyl ester, caffeic acid butyl ester and caffeic acid pentyl ester.
② Caffeic acid derivatives of the formula

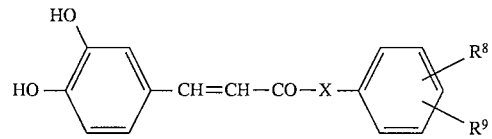

wherein each of $R^8$ and $R^9$ is hydrogen atom, an alkoxy having 1 to 4 carbon atoms or hydroxyl and X is a group of the formula —O—CH$_2$—CH=CH—, —NH—CH$_2$—CH=CH—, —CH$_2$—CH$_2$—CH=CH— or —NH—(CH$_2$)$_n$— (n is 1 to 4) (U.S. Pat. No. 4,733,002, EP 163270).

When $R^8$ and $R^9$ are hydroxyls, they are preferably at the meta- and para-positions. As such compounds, the following can be mentioned.

Caffeic acid-3,4-dihydrocinnamyl ester

Caffeic acid benzylamide
③ Caffeic acid derivatives of the formula

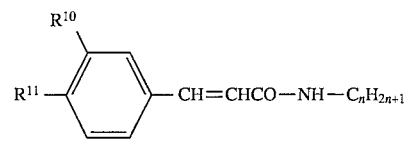

wherein $R^{10}$ and $R^{11}$ are respectively hydroxyl or an alkoxy having 1 to 4 carbon atoms, and n is an integer of 6 to 14 (U.S. Pat. No. 4,733,002, EP 163270).

As such compounds, the following can be shown.

Caffeic acid hexylamide

Caffeic acid octylamide

Caffeic acid decylamide 3,4-Dimethoxycinnamic acid octylamide
④ Aromatic unsaturated ketone compounds of the formula

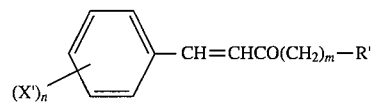

wherein R' is hydroxyl, a phenyl which may be substituted by a lower alkoxy or a halogen atom, specifically chlorine atom, or hydrogen atom, m is an integer of 0 to 7 where it is an integer of 1 to 7 particularly 3 to 7 when R' is hydrogen atom and 0 to 3 when R' is a phenyl which may be substituted, n is 2 or 3 and X' is hydroxyl or a lower alkoxy adjacent to each other (U.S. Pat. No. 4,733,002, EP 163270).

As such compounds, the following can be shown.

1-(3',4'-Dihydroxyphenyl)-3-oxo-1-octene 1,5-bis(3',4'-Dihydroxyphenyl)-3-oxo-1-pentene 1-(3',4'-Bistetrahydropyranyloxyphenyl)-6-(3",4"-dimethoxy-phenyl)-3-oxo-1-hexene ⑤ Substituted stylene derivatives of the formula

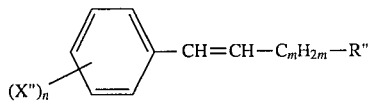

wherein R" is hydrogen atom or

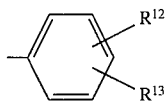

where $R^{12}$ and $R^{13}$ are respectively hydrogen atom, hydroxyl, a lower alkoxy having 1 to 4 carbon atoms or a halogen atom, specifically chlorine atom, m is an integer of 1 to 8, particularly 3 to 7 when R" is hydrogen atom and an integer of 0 to 5, particularly 1 to 3 when R" is

n is 2 or 3 and X" is hydroxyl or a lower alkoxy having 1 to 4 carbon atoms which is adjacent to each other (U.S. Pat. No. 4,733,002, EP 163270).

As such compounds, the following can be shown.

1-(3',4'-Dihydroxyphenyl)-1-hexene 1-(3',4'-Dihydroxyphenyl)-1-heptene 1-(3',4'-Dihydroxyphenyl)-1-octene 1-(3',4'-Dihydroxyphenyl)-4-phenyl-1-butene 1-(3',4'-Dihydroxyphenyl)-4-(3",4"-dimethoxyphenyl)-1butene ⑥ Aromatic compounds of the formula

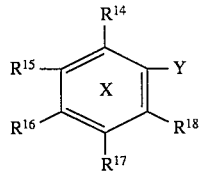

wherein Y is —CH=CH—CONH—D, —C≡C—E, —CH=CH—CO—O—$C_{1-3}$alkylene

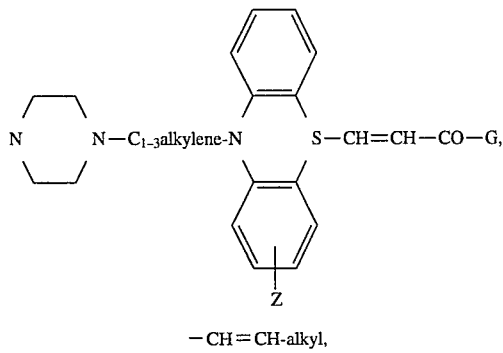

—CH=CH—CO-alkyl, an alkyl having 3 or more carbon atoms which may be substituted by hydroxyl or an alkoxycarbonyl, an alkylcarbonyl which may be substituted by carboxyl or —CO—NH—J where D is an alkyl having 4 to 8 carbon atoms, a phenyl which may be substituted by carboxyl or an alkoxy having 1 to 4 carbon atoms, a heterocycle-alkyl ($C_{1-4}$) or an aralkyl (where the alkylene moiety of the aralkyl is substituted by hydroxyl), E is an alkyl having 4 to 8 carbon atoms or an alkyl ($C_{5-7}$)-carbonyl, G is hydroxyl, an alkyl having 2 to 7 carbon atoms substituted by carboxyl or amino which may be substituted by a mono- or di-alkyl($C_{1-4}$) or phenyl substituted by carboxyl, J is

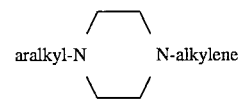

which may be substituted by a halogen or carboxyphenyl and Z is a halogen atom; and $R^{14}$, $R^{15}$, $R^{16}$, $R^{17}$ and $R^{18}$ are respectively hydrogen atom, hydroxyl, an aliphatic hydrocarbon residue having 3 or less carbon atoms and single or double bonds, (which may be substituted by hydroxyl), a carboxylalkyl or a lower alkoxy where $R^{15}$ and $R^{16}$ may form a naphthyl combinedly with the benzene ring X (the naphthyl is substituted by a group selected from hydroxyl and alkoxy); with the proviso that when Y is —CH=CH—CO—alkyl, one of $R^{14}$, $R^{15}$, $R^{16}$, $R^{17}$ and $R^{18}$ is a carboxyalkyl, an aliphatic hydrocarbon residue having 3 or less carbon atoms and single or double bonds, (which may be substituted by hydroxyl), or two of $R^{14}$, $R^{15}$, $R^{16}$, $R^{17}$ and $R^{18}$ are hydroxyls which are not adjacent to each other, and when Y is —CH=CH—alkyl, one of $R^{14}$, $R^{15}$, $R^{16}$, $R^{17}$ and $R^{18}$ is an alky substituted by hydroxyl, or their pharmacologically acceptable salts (U.S. Pat. No. 4,733,002, EP 163270).

The heterocycle of the heterocycle-alkyl represented by D preferably contains 1 or 2 nitrogen, oxygen or sulfur atom as a hetero atom and is a 5- or 6-membered monocyclic heterocycle. The heterocycle may have a substituent on the ring, and examples of the substituent include hydroxyl, oxo and halogen.

The alkyl moiety of the aralkyl group represented by D is preferably those having 1 to 3 carbon atoms, with preference given to those where the carbon atom which binds to the aryl group is substituted by one hydroxyl.

The aryl moiety of the aralkyl in

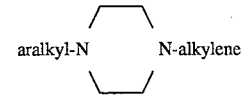

represented by J which may be substituted by a halogen, is preferably phenyl or a phenyl substituted by hydroxyl, halogen, etc., and the alkyl moiety is preferably those having 1 to 3 carbon atoms. The alkyl moiety may be substituted by phenyl. The alkylene moiety includes those having 2 to 3 carbon atoms.

The alkyl moiety in —CH=CH-alkyl represented by Y includes those having 4 to 6 carbon atoms.

The alkyl moiety in —CH=CH—CO-alkyl represented by Y includes those having 4 to 6 carbon atoms.

The alkoxycarbonyl in the alkyl having 3 or more carbon atoms represented by Y, which may be substituted by hydroxyl or alkoxycarbonyl is preferably those having 2 to 5 carbon atoms, and the alkyl having 3 or more carbon atoms includes those having 3 to 8 carbon atoms, and a carbon atom adjacent to the X ring is preferably substituted by hydroxyl, and the alkoxycarbonyl is preferably the terminal carbon atom of the alkyl having 3 or more carbon atoms. The alkyl having 3 or more carbon atoms is preferably a straight chain.

As regards the alkylcarbonyl represented by Y, which may be substituted by carboxyl, the alkyl moiety of the alkylcarbonyl is preferably those having 1 to 4 carbon atoms and a straight chain.

The aliphatic hydrocarbon residue having 3 or less carbon atoms represented by $R^{14}$ to $R^{18}$, which comprises single bonds or double bonds and may be substituted by hydroxyl includes alkyl, alkenyl and hydroxyl-substituted alkyl. The alkyl moiety of the carboxyalkyl represented by $R^{14}$ to $R^{18}$ is preferably those having 3 or less carbon atoms, and examples of the carboxyalkyl include carboxymethyl, carboxyethyl and carboxypropyl. The alkoxy represented by $R^{14}$ to $R^{18}$ is preferably those having 1 to 5 carbon atoms.

When $R^{15}$ and $R^{16}$ combinedly form a naphthyl with the benzene ring, the alkoxy to be substituted preferably has carbon atoms of 3 or below. The substituent on the naphthyl may be at any optional position of the naphthalene skeleton, with preference given to the 2- and/or 3-position.

As such compounds, the following can be shown.

Caffeic acid p-n-butylanilide
Caffeic acid m-n-octylanilide
Caffeic acid 3,4-dimethoxyanilide
Caffeic acid 2-(2-pyridyl)ethylamide
Caffeic acid 3-morpholinopropylamide
Caffeic acid 3-(2-oxo-3-pyrrolidinyl)propylamide
Caffeic acid norephedrinamide
3,4-Dimethoxy cinnamic acid norephedrinamide
3,4-Dimethoxy perphenazine cinnamate
1-(3,4-Dihydroxyphenyl)octan-1-ol
1-(3,4-Dihydroxyphenyl)hexan-1-ol
1-(3,4-Dihydroxyphenyl)butan-1-ol
4-Octylcatechol
4-Hexylcatechol
4-Butylcatechol
1-(3,4-Dimethoxyphenyl)-1-octyne
1-(3,4-Dihydroxyphenyl)-1-octyne
1-(3,4-Dihydroxyphenyl)-1-hexyne
1-(3,4-Dihydroxyphenyl)-1-butyne
1-(3,4-Dimethoxyphenyl)-1-decyn-3-one
1-(3,4-Dihydroxyphenyl)-1-octyn-3-one
1-(3,4-Dihydroxyphenyl)-8-hydroxy-3-oxo-1-octene
1-(3,4-Dihydcoxyphenyl)-6-oxo-7-octene acid
1-(3,4-Dihydroxyphenyl)-8-dimethylamino-1-octen-3-one
1-(3,4-Dihydroxy-2-propylphenyl)-3-oxo-1-octene
1-[5-(2-Propenyl)-3,4-dihydroxyphenyl ]1-octen-3-one
Ethyl 2,3-dimethoxynaphthalene-7-carboxylic acid 4-[α-(p-chlorophenyl)benzyl]-1-piperadinylamide
Ethyl 2,3-dihydroxynaphthalene-7-carboxylic acid 2-[4{α-(p-chlorophenyl)}benzyl]piperadinylamide
2,3-Dihydroxynaphthalene-7-carboxylic acid o-carboxyphenylamide
4-(2,3-Dihydroxynaphthalen-7-yl)-4-oxobutyric acid
2,3-Dihydroxy-7-(1-oxobutyl)naphthalene
2,3-Dihydroxy-7-butylnaphthalene
Ethyl 4-(2,3-dihydroxynaphthalen-7-yl)-butyrate
1-[2-(2-Carboxyethyl)-3,4-dihydroxyphenyl]-3-oxo-1-octene
1-(2,4-Dihydroxyphenyl)-1-octen-3-one
1-(2,5-Dihydroxyphenyl)-1-octen-3-one
1-(3,5-Dihydroxyphenyl)-1-octen-3-one
3,4-Dihydroxy-2'-carboxychalcone
3,4-Dihydroxy-4'-carboxychalcone
1-(2-Hydroxy-3-hydroxymethylphenyl)-1-octen-3-one
1-(3-Hydroxy-2-hydroxymethylphenyl)-1-octen-3-one
1-(3-Hydroxy-4-hydroxymethylphenyl)-1-octen-3-one
1-(4-Hydroxy-3-hydroxymethylphenyl)-1-octen-3-one
1-(4-Hydroxy-3-hydroxymethylphenyl)-1-hexene
N-(4'-Hydroxy-3'-hydroxymethylcinnamoyl)anthranilic acid ⑦ Bis-S-alkylbenzene derivatives of the formula

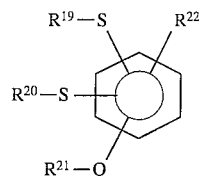

wherein each of $R^{19}$ and $R^°$ is an alkyl having 1 to 4 carbon atoms, $R^{21}$ is hydrogen atom, an alkyl having 1 to 4 carbon atoms, an acyl having 1 to 5 carbon atoms, an alkoxyalkyl, an alkylcarbamoyl or a phosphate residue and $R^{22}$ is a group of the formula —$C_mH_{2m}$—$R^{23}$ where $R^{23}$ is hydrogen atom or a cycloalkyl having 5 to 7 carbon atoms which may be substituted by hydroxyl and m is an integer of 3 to 15, a substituent of the formula —$C_nH_{2n}$—$R^{24}$ where $R^{24}$ is hydrogen atom, an acyl having 1 to 5 carbon atoms or an alkyl having 1 to 4 carbon atoms which may be substituted by hydroxyl and n is an integer of 3 to 15, or a benzhydrylpiperazylalkyl (U.S. Pat. No. 4,933,329, EP 319947).

The alkyl and the alkoxy are not particularly limited as long as they have 1 to 4 carbon atoms.

The alkoxy and alkyl moieties in the alkoxyalkyl have 1 to 4 carbon atoms each, and include, for example, methoxymethyl.

The alkyl moiety in the alkylcarbamoyl has 1 to 4 carbon atoms and examples thereof include methylcarbamoyl, ethylcarbamoyl and propylcarbamoyl.

The alkyl moiety in the benzhydrylpiperazylalkyl has 1 to 4 carbon atoms and examples thereof include benzhydrylpiperazylmethyl, and so on.

It is preferable that the substituents $R^{19}$—S and $R^{20}$—S on the phenyl ring be at the meta-position to each other.

In particular, the substituent $R^{21}$—O in the following formula is preferably at the ortho-position to each of the other two substituents mentioned above. Namely, compounds of the following formula are particularly preferable.

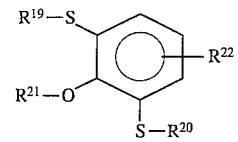

wherein $R^{19}$, $R^{20}$, $R^{21}$ and $R^{22}$ are as defined above.

Particularly preferred positions are $R^{21}$—O at the 1-, $R^{19}$—S at the 2, $R^{22}$ at the 4and S—$R^{20}$ at the 6-positions. Namely, compounds of the following formula are particularly preferable.

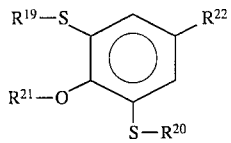

wherein $R^{19}$, $R^{20}$, $R^{12}$ and $R^{22}$ are as defined above.
As such compounds, the following can be shown.

8-{3,5-bis(Methylthio)-4-hydroxyphenyl} octanol 2,6-bis(Methylthio)-4-octylphenol 2,6-bis(Methylthio)-4-octylannisole 2,6-bis(Methylthio)-4-octylphenyl-N-isopropylcarbamate 2,6-bis(Methylthio)-4-octylphenyl-N-methylcarbamate 2,6-bis(Methylthio)-4-octylphenyl-acetate 2,6-bis(Methylthio)-4-octylphenyl-phosphate 4-[5-(4-Methoxymethoxyphenyl)pentyl]-cyclohexanol cis-4-[5-(3,5-bis(Methylthio)-4-hydroxyphenyl)pentyl] cyclohexanol trans-4-[5-(3,5-bis(Methylthio)-4-hydroxyphenyl)pentyl] cyclohexanol 2,6-bis(Methylthio)-4-(8-methoxyoctyl)phenol 2,6-bis(Methylthio)-4-{8-(2-hydroxyethoxy)octyl}phenol 3,5-bis(Methylthio)-4-methoxymethoxybenzaldehyde propyleneacetal 1-{3,5-bis(sec-Butylthio)-4-hydroxyphenylmethyl}-4-(1, 1diphenylmethyl)piperazine The fatty acid monoglyceride is a monoester of fatty acid and glycerin where the fatty acid preferably has 14 to 28 carbon atoms, more preferably 16 to 18 carbon atoms and the number of unsaturated bonds, particularly double bonds, when the fatty acid is unsaturated is 1 or 2. Specific examples of unsaturated fatty acid include palmitoleic acid, oleic acid, linoleic acid, linolenic acid, or the like, and examples of saturated fatty acid include myristic acid, palmitic acid, stearic acid, behenic acid, hepta-cosanoic acid, or the like. As the fatty acid, those having the above carbon atoms may be used solely or in mixture, with preference given to unsaturated fatty acids.

In the present invention, the fatty acid moiety of the polyoxyethylenesorbitan fatty acid ester preferably has 10 to 18 carbon atoms, which is exemplified by polyoxyethylenesorbitan fatty acid esters such as polyoxyethylenesorbitan monooleate, polyoxyethylenesorbitan monostearate, polyoxyethylenesorbitan monopalmitate, polyoxyethylenesorbitan monolaurate, or the like.

Further, a nonionic surfactant other than the above-mentioned polyoxyethylenesorbitan fatty acid esters may be co-used, and examples of such surfactants include polyoxyethylenesorbit fatty acid ester, polyoxyethylene hydrogenated castor oil, polyglycerin fatty acid ester, or the like. The nonionic surfactant to be used in the present invention is not particularly limited and those acceptable as pharmaceutical additives may be used. The HLB value (hydrophile-lipophile balance) is preferably not less than 3, preferably 10 to 20.

The solubility of the slightly water-soluble drug in a fatty acid monoglyceride and a nonionic surfactant is about 10–500 mg/ml.

No limitation is posed on the porous inorganic substance of the present invention as long as the substance efficiently adsorbs the non-micelle compositions obtained by adding a fatty acid monoglyceride and/or a polyoxyethylenesorbitan fatty acid ester and is pharmacologically acceptable, and examples include magnesium aluminate silicate, silicon dioxides such as light silicic acid anhydride and silicon dioxide hydrate, or the like.

The proportion of each ingredient in the non-micelle pharmaceutical compositions for oral administration is not particularly limited but adjusted suitably depending on the kind of tile slightly water-soluble drug.

For example, when either the fatty acid monoglyceride or the polyoxyethylenesorbitan fatty acid ester is used solely, it is preferably used in an amount of 1 to 100 parts by weight, preferably 5 to 60 parts by weight per 1 part by weight of the slightly water-soluble drug. When the fatty acid monoglyceride and the polyoxyethylenesorbitan fatty acid ester are used combinedly, they are preferably used in an amount of 1 to 100 parts by weight, preferably 10 to 50 parts by weight per 1 part by weight of the slightly water-soluble drug.

Further, when a nonionic surfactant other than the polyoxyethylenesorbitan fatty acid ester is also used, a fatty acid monoglyceride and/or a polyoxyethylenesorbitan fatty acid ester and a nonionic surfactant are used in an amount of 1 to 100 parts by weight, preferably 10 to 50 parts by weight per 1 part by weight of the slightly water-soluble drug.

In the pharmaceutical composition for oral use prepared by adsorption onto the porous inorganic substance, the porous inorganic substance is used in an amount of 1 to 100 parts by weight, preferably 2 to 10 parts by weight per 10 parts by weight of the aforementioned non-micelle pharmaceutical composition for oral use.

The non-micelle pharmaceutical compositions of the present invention are normally prepared by dissolving a slightly water-soluble drug in a fatty acid monoglyceride and/or a polyoxyethylenesorbitan fatty acid ester, and a nonionic surfactant other than the polyoxyethylenesorbitan fatty acid ester. Other additives such as stabilizers, antiseptics, extenders, etc. may be further added to the composition. The composition is normally formulated into capsule preparations, specifically into soft capsules.

The pharmaceutical compositions prepared by adsorption onto a porous inorganic substance are normally prepared in the form of powders and granules and the adsorption is conducted by a method known per se. That is, the pharmaceutical composition comprising adsorption onto a porous inorganic substance is prepared by mixing a non-micelle pharmaceutical composition for oral use of the present invention with a porous inorganic substance. The powders thus obtained may be formulated into powder preparations by adding an excipient for formulation such as mannitol, etc., packed in capsules or tableted by a conventional method.

EXAMPLE 1

2-[p-(4-Benzhydrylpiperadinophenyl)ethyl methyl 2,6-dimethyl-4-(3-nitrophenyl)-1,4-dihydropyridine-3,5-dicarboxylate] hydrochloride (20.1 g) is added to unsaturated fatty acid monoglyceride (Kao, "Excel O-95R", 650 g), followed by dissolution and stirring at 40° C. to give a non-micelle solution.

EXAMPLE 2

2-[p-(4-Benzhydrylpiperadinophenyl)ethyl methyl 2,6-dimethyl-4-(3-nitrophenyl)-1,4-dihydropyridine-3,5-dicarboxylate] hydrochloride (20.1 g) is added to polyoxyethylenesorbitan monooleate (Nikko Chemical, "TO-10M", 650 g), followed by dissolution and stirring at 40° C. to give a non-micelle solution.

EXAMPLE 3

2-[p-(4-Benzhydrylpiperadinophenyl)ethyl methyl 2,6-dimethyl-4-(3-nitrophenyl)-1,4-dihydropyridine-3,5-dicarboxylate] hydrochloride (20.1 g) is added to a mixture of unsaturated fatty acid monoglyceride (Kao, "Excel O-95R") and polyoxyethylenesorbitan monooleate (Nikko Chemical, "TO-10M") in a proportion of 1:1 (650 g), followed by dissolution and stirring at 40° C. to give a non-micelle solution.

EXAMPLE 4

2-[p-(4-Benzhydrylpiperadinophenyl)ethyl methyl 2,6-dimethyl-4-(3-nitrophenyl)-1,4-dihydropyridine-3,5-dicarboxylate] hydrochloride (20.1 g) is added to a mixture of unsaturated fatty acid monoglyceride (Kao, "Excel O-95R") and polyethylene glycol (PEG 400) in a proportion of 1:1 (650 g), followed by dissolution and stirring at 40° C. to give a non-micelle solution.

COMPARISON EXAMPLE 1

2-[p-(4-Benzhydrylpiperadinophenyl)ethyl methyl 2,6-dimethyl-4-(3-nitrophenyl)-1,4-dihydropyridine-3,5-dicarboxylate] hydrochloride (20.1 g) is added to polyethylene glycol (PEG 400, 650 g), followed by dissolution and stirring at 40° C. to give a non-micelle solution.

COMPARISON EXAMPLE 2

2-[p-(4-Benzhydrylpiperadinophenyl)ethyl methyl 2,6-dimethyl-4-(3-nitrophenyl)-1,4-dihydropyridine-3,5-dicarboylate] hydrochloride (10 g) is pulverized with a mortar and mixed with lactose (190 g) to give 200 g of a powder for capsules.

EXAMPLE 5

2-[p-(4-Benzhydrylpiperadinophenyl)ethyl methyl 2,6-dimethyl-4-(3-nitrophenyl)-1,4- dihydropyridine-3,5-dicarboxylate] hydrochloride (20.1 g) is added to unsaturated fatty acid monoglyceride (Kao, "Excel O-95R", 650 g), followed by dissolution and stirring at 40° C. to give a non-micelle solution. The thus-obtained solution (600 g) and magnesium alminate metasilicate (Fuji Kagaku Sangyo, "Neusilin US$_2$", 370 g) are mixed with a stirring-granulator. Thereto is added Carmellose sodium A type (30 g) for mixing and stirring, followed by addition of purified water (250 ml) to give granules. The granules are dried at 40° C. for 17 hours with a forced-air drier and passed through a sieve of 42–200 mesh to give 550 g of fine granules for capsules.

EXAMPLE 6

2-[p-(4-Benzhydrylpiperadinophenyl)ethyl methyl 2,6-dimethyl-4-(3-nitrophenyl)-1,4-dihydropyridine -3,5-dicarboxylate] hydrochloride (20.1 g) is added to polyoxyethylcnesorbitan monooleate (Nikko Chemical, "TO10M", 650 g), followed by dissolution and stirring at 40° C. to give a non-micelle solution. The thus-obtained solution (600 g) and magnesium alminate metasilicate (Fuji Kagaku Sangyo, "Neusilin US$_2$", 370 g) are mixed with a stirring-granulator. Thereto is added Carmellose sodium A type (30 g) for mixing and stirring, followed by addition of purified water (250 ml) to give granules. The granules are dried at 40° C. for 17 hours with a forced-air drier and passed through a sieve of 42–200 mesh to give 550 g of fine granules for capsules.

EXAMPLE 7

2-[p-(4-Benzhydrylpiperadinophenyl)ethyl methyl 2,6-dimethyl-4-(3-nitrophenyl)-1,4-dihydropyridine-3,5-dicarboxylate] hydrochloride (20.1 g) is added to a mixture of unsaturated fatty acid monoglyceride (Kao, "Excel O-95R") and polyoxyethylenesorbitan monooleate (Nikko Chemical, "TO-10M") in a proportion of 1:1 (650 g), followed by dissolution and stirring at 40° C. to give a non-micelle solution. The thus-obtained solution (600 g) and magnesium alminate metasilicate (Fuji Kagaku Sangyo, "Neusilin US$_2$", 370 g) are mixed with a stirring-granulator. Thereto is added Carmellose sodium A type (30 g) for mixing and stirring, followed by addition of purified water (250 ml) to give granules. The granules are dried at 40° C. for 17 hours with a forced-air drier and passed through a sieve of 42–200 mesh to give 550 g of fine granules for capsules.

EXPERIMENT EXAMPLE 1

Absorption by Oral Administration

The absorption and stability of the pharmaceutical compositions as obtained in Examples 1 to 7 and Comparison Examples 1 and 2 are summarized in Table 1.

The absorption evaluation was conducted as follows. That is, a composition of the present invention was administered to a beagle weighing about 10 kg after fasted for 20 hours before the administration in a dose of 3 mg/0.1 ml/kg, and sample blood was taken from radialis cutaneous vein at given time intervals up to 24 hours after the administrations. The plasma of the blood sample was centrifuged, deproteinized with acetonitrile and determined by high performance liquid chromatography (HPLC) using a reversed-phase column [ODS ($C_{18}$), 4 µ, 3.9 φ×150 mm, Japan Waters]. The BA% was estimated on the basis of the blood concentration.

TABLE 1

|  | Additives used | Absorption (BA %) |
|---|---|---|
| Ex. 1 | Excel O-95R | 26.0 |
| Ex. 2 | TO-10M | 24.3 |
| Ex. 3 | Excel O-95R + TO-10M (1:1) | 25.6 |
| Ex. 4 | PEG 400 + Excel O-95R (1:1) | 21.7 |
| Ex. 5 | Excel O-95R/Neusilin | 23.0 |
| Ex. 7 | Excel O-95R + TO-10M (1:1)/ Neusilin | 29.4 |
| Comp. Ex. 1 | PEG 400 | 1.2 |
| Comp. Ex. 2 | no additive | 0.3 |

EXPERIMENT EXAMPLE 2

Stability of the Pharmaceutical Composition of the Invention

Using the pharmaceutical compositions as prepared in Examples 5 to 7, tile stability was examined by a storage test at 40° C. The content of analogous substance and appearance 4 weeks later are summarized in Table 2.

TABLE 2

| Additives used | Stability (60° C., 4 weeks) | |
|---|---|---|
| | content of analogous substance (%)* | appearance |
| Excel O-95R/Neusilin (Ex. 5) | 2.9 | colored |
| TO-10M/Neusilin (Ex. 6) | 1.2 | no change |
| Excel O-95R + TO-10M (1:1)/Neusilin (Ex. 7) | 1.6 | no change |

*: dihydropyridine decomposing substance

The pharmaceutical compositions for oral administration of the present invention markedly improve absorption of slightly water-soluble drugs such as dihydropyridine, etc. as evidenced in Experiment Example 1 and the stability of the slightly water-soluble drugs in a powdery form is excellent as evidenced in Experiment Example 2.

The use of the pharmaceutical compositions for oral administration of the present invention enables decreasing of the dose amount of slightly water-soluble drugs, which eventually leads to alleviation of pains and side effects on the part of patients.

What is claimed is:

1. A non-micelle pharmaceutical composition for oral administration comprising a dihydropyridine derivative of the formula

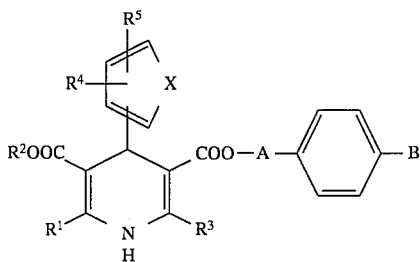

wherein $R^1$, $R^2$, and $R^3$ are the same or different and are an alkyl, a cycloalkyl or an alkoxyalkyl, $R^4$ and $R^5$ are the same or different and are hydrogen atom, a halogen, nitro, a halogenated alkyl, an alkylsulfonyl, a halogenated alkoxy, an alkylsulfinyl, an alkyl, a cycloalkyl, an alkoxy, cyano, an alkoxycarbonyl or an alkylthio wherein $R^4$ and $R^5$ are not hydrogen atoms at the same time, X is a group of vinylene or azomethine, A is an alkylene and B is $-N(R^6)_2$ or

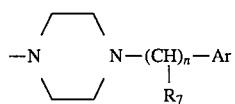

wherein $R^6$ and $R^7$ are respectively hydrogen atom, an alkyl, a cycloalkyl, an aralkyl, an aryl or pyridyl, Ar is an aryl or pyridyl and n is an integer of 0 to 2, or their acid addition salts dissolved in a polyoxyethylenesorbitan fatty acid ester and a fatty acid monoglyceride.

2. A pharmaceutical composition for oral administration as claimed in claim 1, wherein the dihydropyridine derivative is selected from the group consisting of 2-(p-Dimethylaminophenyl)ethyl methyl 2,6-dimethyl-4-(4-cyano-2-pyridyl)-1,4-dihydropyridine-3,5-dicarboxylate and its hydrochloride, 2-(p-Dimethylaminophenyl)ethyl methyl 2,6-dimethyl-4-(2-triflouromethyl-3-pyridyl)-1,4-dihydropyridine-3,5-dicarboxylate and its hydrochloride, 2-(p-Dibenzylaminophenyl)ethyl methyl 2,6-dimethyl-4-(4-cyano-2-pyridyl)-1,4-dihydropyridine-3,5-dicarboxylate and its hydrochloride, 2-(p-Dibenzylaminophenyl)ethyl methyl 2,6-dimethyl-4-(2-trifluoromethyl-3-pyridyl)-1,4-dihydropyridine-3,5-dicarboxylate and its hydrochloride, 2-[p-(4-Benzhydrylpiperadino)phenyl]ethyl methyl 2,6-dimethyl-4(4-cyano-2-pyridyl)-1,4-dihydropyridine-3,5-dicarboxylate and its hydrochloride, 2-[p-(4-Benzhydrylpiperadino)phenyl]ethyl methyl 2,6-dimethyl-4-(2-trifluoromethyl-3-pyridyl)-1,4-dihydropyridine-3,5-dicarboxylate and its fumarate, and 2-[p-(4-Benzhydrylpiperadino)phenyl]ethyl methyl 2,6-dimethyl-4-(3-nitrophenyl)-1,4-dihydropyridine-3,5-dicarboxylate and its hydrochloride.

3. A pharmaceutical composition for oral administration as claimed in claim 1, wherein the fatty acid monoglyceride is of a fatty acid having 14 to 28 carbon atoms.

4. A pharmaceutical composition for oral administration as claimed in claim 3 wherein the fatty acid having 14 to 28 carbon atoms is selected from the group consisting of palmitoleic acid, oleic acid, linoleic acid and linolenic acid.

5. A pharmaceutical composition for oral administration as claimed in claim 1, wherein the polyoxyethylenesorbitan fatty acid ester is of a fatty acid having 10 to 18 carbon atoms.

6. A pharmaceutical composition for oral administration as claimed in claim 5, wherein the polyoxyethylenesorbitan fatty acid ester is selected from the group consisting of polyoxyethylenesorbitan monooleate, polyoxyethylenesorbitan monostearate, polyoxyethylenesorbitan monopalmitate and polyoxyethylenesorbitan monolaurate.

7. A pharmaceutical composition for oral administration as claimed in claim 1, wherein the fatty acid monoglyceride and the polyoxyethylenesorbitan fatty acid ester are present in an amount of 1 to 100 parts by weight per 1 part by weight of drug.

8. A pharmaceutical composition for oral administration as claimed in claim 1, which further comprises a nonionic surfactant of HLB (hydrophile-lipophile balance) not less than 3 other than a polyoxyethylenesorbitan fatty acid ester.

9. A pharmaceutical composition for oral administration as claimed in claim 8, wherein the nonionic surfactant is selected from the group consisting of polyoxyethylene hydrogenated castor oil and polyglycerin fatty acid ester.

10. A pharmaceutical composition for oral administration as claimed in claim 8, wherein the fatty acid monoglyceride, the polyoxyethylenesorbitan fatty acid ester and the nonionic surfactant other than polyoxyethylenesorbitan fatty acid ester are present in an amount of 1 to 100 parts by weight per 1 part by weight of a slightly water-soluble drug.

11. A pharmaceutical composition for oral administration as claimed in claim 1, wherein the dihydropyridine derivative is 2-[p-(4-benzhydrylpiperazino)phenyl]ethyl methyl 2,6-dimethyl-4-(3-nitrophenyl)-1,4-dihydropyridine-3,5-dicarboxylate hydrochloride.

* * * * *